US00PP33167P2

(12) United States Plant Patent
van der Arend

(10) Patent No.: US PP33,167 P2
(45) Date of Patent: Jun. 15, 2021

(54) ***ALOCASIA* PLANT NAMED 'PPIALO008'**

(50) Latin Name: *Alocasia brancifolia*
Varietal Denomination: PPIALO008

(71) Applicant: Rene P. A. van der Arend, Naaldwijk (NL)

(72) Inventor: Rene P. A. van der Arend, Naaldwijk (NL)

(73) Assignee: Plant Planet International B.V., Naaldwijk (NL)

( * ) Notice: Subject to any disclaimer, the term of this patent is extended or adjusted under 35 U.S.C. 154(b) by 0 days.

(21) Appl. No.: 16/974,059

(22) Filed: Sep. 18, 2020

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 6/10; A01H 5/12
See application file for complete search history.

*Primary Examiner* — Keith O. Robinson
(74) *Attorney, Agent, or Firm* — C. Anne Whealy

(57) ABSTRACT

A new and distinct cultivar of *Alocasia* plant named 'PPIAL0008', characterized by its broadly upright to spreading plant habit; moderately vigorous to vigorous growth habit; large pinnatisect leaves that are dark green in color; and pink-colored leaf petioles with dark green-colored blotches and marbling.

2 Drawing Sheets

Botanical designation: *Alocasia brancifolia.*
Cultivar denomination: 'PPIAL0008'.

STATEMENT REGARDING PRIOR DISCLOSURES BY INVENTOR/APPLICANT & ASSIGNEE

An European Community Plant Breeder's Rights application for the instant plant was filed by the Assignee, Plant Planet International B.V. of Naaldwijk, The Netherlands on Nov. 28, 2019, application number 2019/3180. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Alocasia* plant, botanically known as *Alocasia brancifolia* and hereinafter referred to by the name 'PPIAL0008'.

The new *Alocasia* plant is a naturally-occurring whole plant mutation of an unnamed selection of *Alocasia brancifolia*, not patented. The new *Alocasia* plant was discovered and selected by the Inventor in February, 2019 as a single plant from within a population of plants of the unnamed selection in a controlled greenhouse environment in Naaldwijk, The Netherlands.

Asexual reproduction of the new *Alocasia* plant by cuttings in a controlled greenhouse environment in Naaldwijk, The Netherlands since April, 2019 has shown that the unique features of this new *Alocasia* plant are stable and reproduced true to type in successive generations of asexual reproduction.

SUMMARY OF THE INVENTION

Plants of the new *Alocasia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'PPIAL0008'. These characteristics in combination distinguish 'PPIAL0008' as a new and distinct *Alocasia* plant:

1. Broadly upright to spreading plant habit.
2. Moderately vigorous to vigorous growth habit.
3. Large pinnatisect leaves that are dark green in color.
4. Pink-colored leaf petioles with dark green-colored blotches and marbling.

Plants of the new *Alocasia* differ from plants of the mutation parent selection primarily in leaf petiole color as plants of the new *Alocasia* have pink-colored leaf petioles with dark green-colored blotches and marbling whereas plants of the mutation parent selection have green-colored leaf petioles.

Plants of the new *Alocasia* can be compared to plants of an unnamed selection of *Alocasia zebrina*, not patented. Plants of the new *Alocasia* differ from plants of the unnamed selection of *Alocasia zebrina* in the following characteristics:

1. Plants of the new *Alocasia* have pinnatisect leaves whereas plants of the unnamed selection of *Alocasia zebrina* have cordate-shaped leaves.
2. Plants of the new *Alocasia* have pink-colored leaf petioles with dark green-colored blotches and marbling whereas plants of the unnamed selection of *Alocasia zebrina* have green-striped leaf petioles.

BRIEF DESCRIPTION OF THE PHOTOGRAPHS

The accompanying photographs illustrate the overall appearance of the new *Alocasia* plant showing the colors as true as it is reasonably possible to obtain in colored reproductions of this type. Colors in the photographs may differ slightly from the color values cited in the detailed botanical description which accurately describe the colors of the new *Alocasia* plant.

The photograph on the first sheet is a side perspective view of a typical plant of 'PPIAL0008' grown in a container.

The photograph on the second sheet is a close-up view of the leaf petioles of a typical plant of 'PPIAL0008'.

DETAILED BOTANICAL DESCRIPTION

The aforementioned photographs and following observations and measurements describe plants grown during the autumn in 19-cm containers in a glass-covered greenhouse in Naaldwijk, The Netherlands and under cultural practices typical of commercial *Alocasia* production. During the production of the plants, day temperatures ranged from 10° C. to 25° C. and night temperatures ranged from 4° C. to 15° C. Plants were 15 weeks old when the photographs and the detailed description were taken. In the following description, color references are made to The Royal Horticultural Society Colour Chart, 2015 Edition, except where general terms of ordinary dictionary significance are used.

Botanical classification: *Alocasia brancifolia* 'PPIAL0008'.

Parentage: Naturally-occurring whole plant mutation of an unnamed selection of *Alocasia brancifolia*, not patented.

Propagation:

*Type*.—By cuttings.

*Time to initiate roots, summer*.—About 10 days at temperatures about 22° C. to 25° C.

*Time to initiate roots, winter*.—About 15 days at temperatures about 20° C. to 22° C.

*Time to produce a rooted young plant, summer*.—About 30 days at temperatures about 22° C. to 25° C.

*Time to produce a rooted young plant, winter*.—About 35 days at temperatures about 20° C. to 22° C.

*Root description*.—Fibrous, medium in thickness; typically white in color, actual color of the roots is dependent on substrate composition, water quality, fertilizers, substrate temperature and age of roots.

*Rooting habit*.—Moderately freely branching; medium density.

Plant description:

*Plant and growth habit*.—Broadly upright and spreading plant habit; moderately vigorous to vigorous growth habit; moderate growth rate; about three clumps per plant develop.

*Plant height*.—About 60 cm.

*Plant diameter or spread*.—About 80 cm.

Leaf description:

*Arrangement*.—Alternate; simple.

*Length*.—About 40.3 cm.

*Width*.—About 31.1 cm.

*Shape*.—Pinnatisect; overall leaf shape, broadly ovate.

*Apex*.—Apiculate to mucronate.

*Base*.—Hastate; lobes free.

*Margin*.—Pinnatisect; moderately undulate.

*Texture and luster, upper surface*.—Smooth, glabrous; moderately glossy.

*Texture and luster, lower surface*.—Smooth, glabrous; slightly glossy.

*Venation pattern*.—Pinnate.

*Color*.—Developing leaves, upper surface: Close to between 137A and 143A. Developing leaves, lower surface: Close to 144A. Fully expanded leaves, upper surface: Close to NN137A; midvein, close to 143A to 143B and secondary veins, close to 137A to 137B. Fully expanded leaves, lower surface: Close to between 138B and 191B; midvein, close to 150D sparsely to moderately blotched and marbled with close to 177A; secondary veins, close to 148C.

*Petioles*.—Length: About 46.7 cm. Diameter: Proximally, about 7 cm and distally, close to 1 cm. Aspect: Erect to outwardly leaning. Strength: Moderately strong; flexible. Texture and luster, upper and lower surfaces: Smooth, glabrous; matte. Wing length: About 22.1 cm. Wing diameter: About 1.1 cm. Wing texture and luster, upper and lower surfaces: Smooth, glabrous; matte. Color, leaf petiole, upper surface: Close to between 69B and 182D and heavily blotched and marbled with close to between 147A and N189A. Color, leaf petiole, lower surface: Close to 201B tinged with close to 69B and 182D and moderately blotched and marbled with close to between 147A and N189A. Color, wing, upper surface: Close to 195C slightly tinged with close to 69C and moderately blotched and marbled with close to between 147A and 197A to darker than between 147A and 197A. Color, wing, lower surface: Close to 201B tinged with close to 69B and 182D and moderately blotched and marbled with close to between 147A and N189A.

Inflorescence description: To date, inflorescence initiation and development has not been observed on plants of the new *Alocasia*.

Pathogen & pest resistance: To date, plants of the new *Alocasia* not been observed to be resistant to pathogens and pests common to *Alocasia* plants.

Temperature tolerance: Plants of the new *Alocasia* have been observed to tolerate temperatures ranging from about 5° C. to about 40° C. and to be suitable for USDA Hardiness Zones 11 to 13.

It is claimed:

1. A new and distinct *Alocasia* plant named 'PPIAL0008' as illustrated and described.

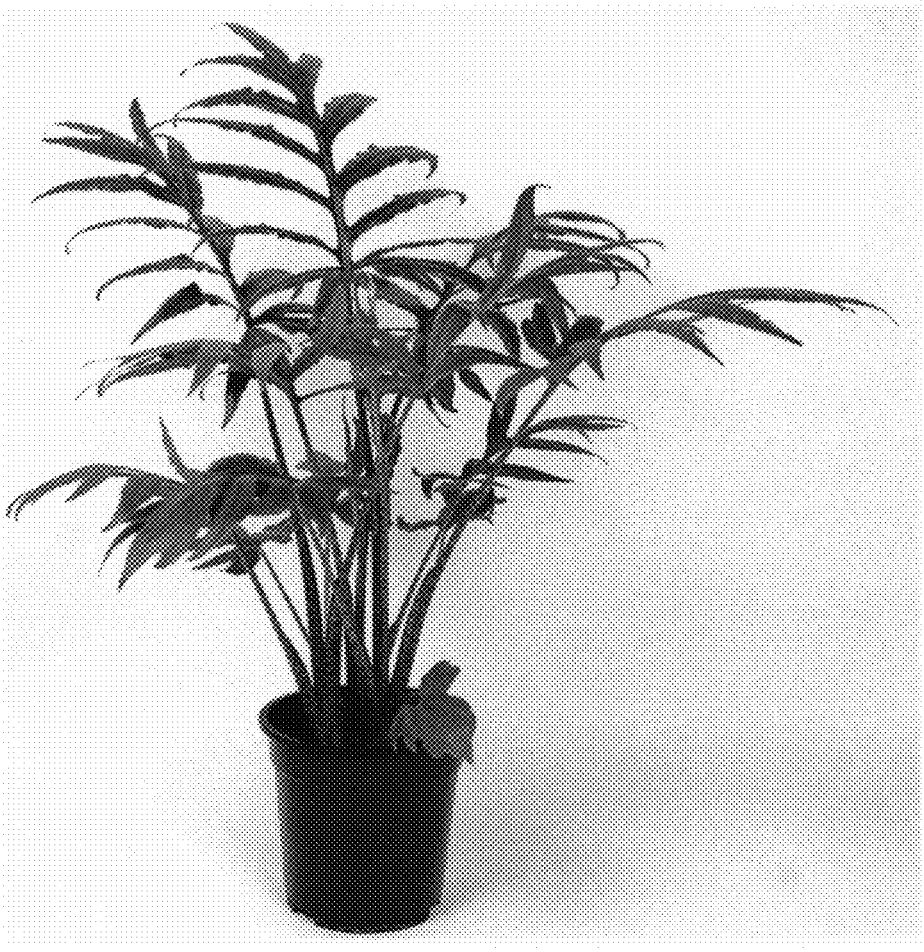

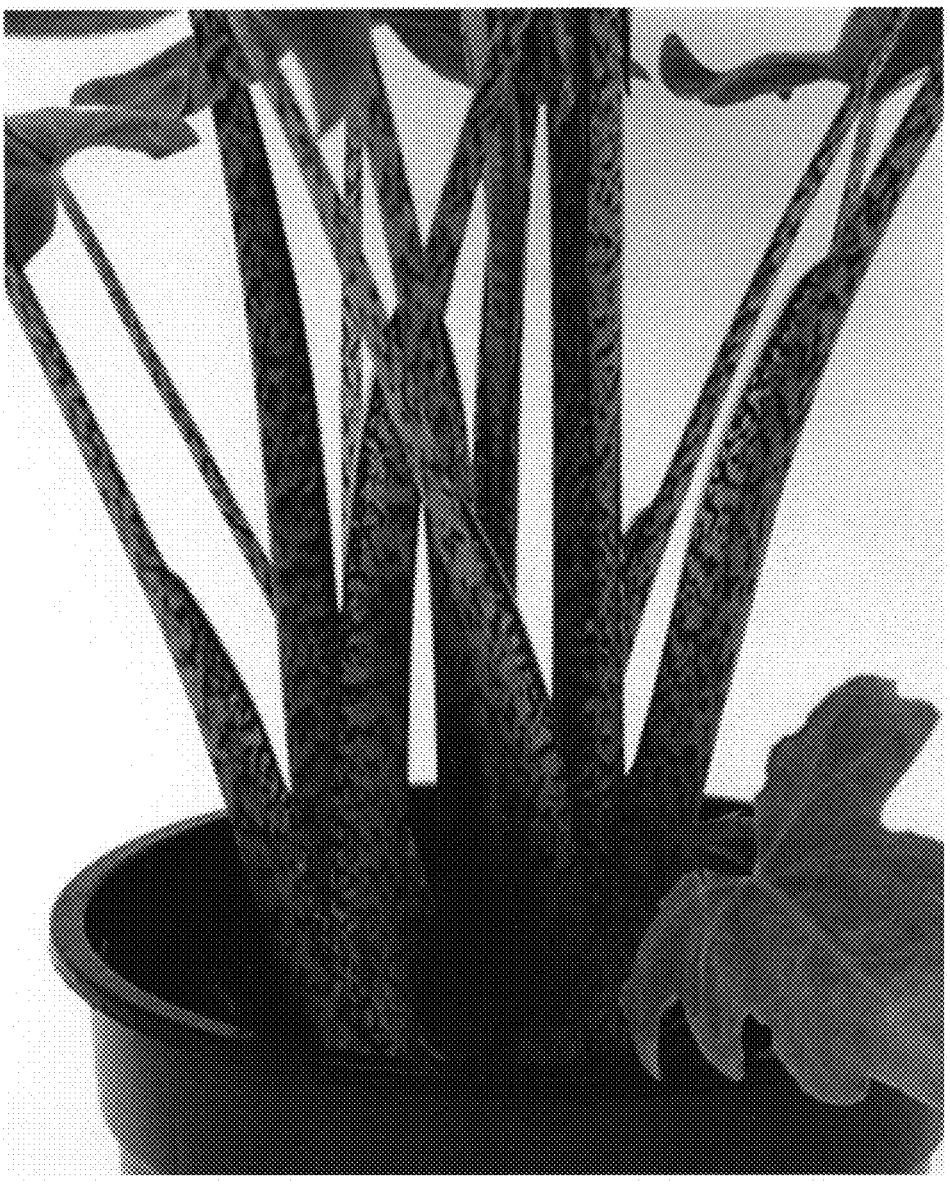

* * * * *